United States Patent [19]

Brader

[11] Patent Number: 4,920,963
[45] Date of Patent: May 1, 1990

[54] APPARATUS FOR PREVENTING BRAIN DAMAGE DURING CARDIAC ARREST, CPR OR SEVERE SHOCK

[76] Inventor: Eric W. Brader, 42 Canter Dr., Sewickley, Pa. 15143

[21] Appl. No.: 177,508

[22] Filed: Apr. 4, 1988

Related U.S. Application Data

[63] Continuation-in-part of Ser. No. 834,341, Feb. 28, 1986, Pat. No. 4,750,493.

[51] Int. Cl.$^5$ ............................................. A61F 7/10
[52] U.S. Cl. .................................... 128/402; 128/380
[58] Field of Search .................. 62/259.3, 4; 128/400, 128/380, 379, 399, 402, 403; 126/204

[56] References Cited

U.S. PATENT DOCUMENTS

| | | | |
|---|---|---|---|
| 2,438,643 | 3/1948 | Moore | 128/399 |
| 3,175,558 | 3/1965 | Caillouette et al. | 126/204 |
| 3,840,918 | 10/1974 | Shave | 128/403 |
| 3,950,158 | 4/1976 | Gossett | 128/403 |
| 4,552,149 | 11/1985 | Tatsuki | 128/402 |
| 4,614,189 | 9/1986 | Mackenzie | 128/380 |

FOREIGN PATENT DOCUMENTS

| | | | |
|---|---|---|---|
| 8204184 | 12/1982 | Australia | 128/400 |
| 0061843 | 10/1982 | European Pat. Off. | 128/400 |
| 454907 | 7/1975 | U.S.S.R. | 128/400 |
| 652942 | 3/1979 | U.S.S.R. | 128/400 |
| 689674 | 10/1979 | U.S.S.R. | 128/400 |
| 995782 | 2/1983 | U.S.S.R. | 128/400 |
| 1138152 | 2/1985 | U.S.S.R. | 128/400 |

*Primary Examiner*—Edward M. Coven
*Assistant Examiner*—Mark J. Graham
*Attorney, Agent, or Firm*—Webb, Burden, Ziesenheim & Webb

[57] ABSTRACT

A method and apparatus for cooling the extracranial area including the face and, optionally, also including the mandible, during emergency care of cardiac arrest or severe shock; the method is preferably implemented by means of a head cooling apparatus which includes a watertight shroud for the head and which needs no refrigeration. The head cooling apparatus contains the unreacted constituents of an endothermic reaction, such as pellets of ammonium nitrate ($NH_4NO_3$) stored adjacent a selectively avaiable reservoir of water, and thus needs no external coolants or refrigeration. Preferably, the head-cooling apparatus comprises a portable, self-contained system which is suitable for storage, transport and/or use anywhere.

14 Claims, 2 Drawing Sheets

APPARATUS FOR PREVENTING BRAIN DAMAGE DURING CARDIAC ARREST, CPR OR SEVERE SHOCK

This application is a continuation-in-part of Application Ser. No. 834,341, filed Feb. 28, 1986 U.S. Pat. No. 4,750,493.

FIELD OF THE INVENTION

The present invention is a method of and apparatus for inhibiting tissue metabolism in the area of the brain and, more particularly, is a method and apparatus for inducing localized hypothermia during the emergency treatment of cardiac arrest or severe shock.

BACKGROUND OF THE INVENTION

Systemic hypothermia can dramatically postpone neurologic deterioration in hypoxic or anoxic tissues. For example, accidental submersion in cold waters, and the commensurate systemic hypothermia thus produced, has consistently contributed to the neurologic survival of accident victims who otherwise would have sustained irreparable brain damage. Observation of this phenomenon led medical practitioners to induce, intentionally, systemic hypothermia in the course of various hypoxia and anoxia-producing surgical procedures, in order to decrease both the systemic metabolism and the associated overall oxygen requirement of the patient.

Whereas systemic hypothermia may be induced without difficulty in the hospital environment, emergency inducement of systemic hypothermia in a non-hospital setting can be difficult or impossible. As a result, induced systemic hypothermia forms no part of, for example, pre-hospital emergency cardiac care such as cardiopulmonary resuscitation (CPR), notwithstanding the beneficial metabolic inhibition which such hypothermia would provide. Similar emergency procedures in which hypothermia has not been induced to date include the pre-hospital emergency care administered to patients in severe shock.

SUMMARY OF THE PRIOR ART

Induced localized hypothermia has been used widely in the non- or pre-hospital treatment of numerous physiologic conditions. Cold packs of some sort are standard equipment in first aid kits, and are used to decrease peripheral blood flow (and commensurate swelling) in the event of contusion, insect bites or stings, nosebleeds, sprains, etc. Cold compresses to the head, of course, have long been a standard symptom-relieving measure for headaches and fever. In addition to these common treatments, however, three of the less well-known uses for topical cold applications are described in U.S. Pat. Nos. 2,438,643, 3,175,558 and 4,552,149.

U.S. Pat. No. 2,438,643 discloses a pack, for use in local refrigeration anesthesia, which contains a plurality of waterproof compartments which contain brine and an absorbent material, such as sawdust. The pack may be cooled in any suitable refrigerating device and then used as a topical cold pack. Because the pack must be refrigerated, its utility for inducing localized hypothermia is limited to those areas for which refrigeration is available.

U.S. Pat. No. 4,552,149 also discloses a coolant-containing, refrigerant-dependent cold pack which is, more specifically, a head coolant device. The device comprises a main body consisting of a cooling piece for covering the top of the head and a plurality of cooling pieces radially arranged around the main body, for covering the front, sides and back of the head. This head cooling cap is designed to inhibit hair loss during the administration of a drug or chemotherapeutic agent for which hair loss is a known side effect. As with all cold packs which require refrigeration, the head coolant device is best suited to hospital and home application, and is not well suited for use in the types of prehospital emergency care for which refrigeration may be unavailable.

U.S. Pat. No. 3,175,558 discloses a thermal therapeutic pack, specifically designed for postpartum application to the female perineum, which contains the unreacted constituents of endothermic reaction. (Similar heat packs may contain the unreacted constituents of an endothermic reaction.) The unreacted constituents are separated by frangible barriers, time-release capsules, or both, and the separation is maintained until the cold pack is needed. At the time of use, the reactants are admixed (by, for example, manually cracking the frangible barrier between them), the endothermic reaction renders the entire cold pack "cold," and the pack is positioned on the patient, as required, to cool the area of application by the reverse conductive heating of the pack by the body. Accordingly, the prior art devices do not provide for, and the existing medical emergency treatments do not accommodate, the inducing of hypothermia (either systemic or localized) in the emergency treatment of cardiac arrest or severe shock. A need therefore remains for a method of inducing sufficient hypothermia in the cardiac arrest or severe shock patient, and an apparatus for accomplishing it, to increase the chances for successful resuscitation unaccompanied by neurologic loss.

BRIEF DESCRIPTION OF THE INVENTION

In order to meet this need, the present invention is a method for cooling the extracranial area including the face and, optionally, also including the mandible, during emergency care of cardiac arrest or severe shock; the method is preferably implemented by means of a head cooling apparatus which includes a watertight shroud for the head and which needs no refrigeration. Extracranial cooling causes two thermal changes in the physiology of the cardiac or respiratory patient: extracranial vasoconstriction promotes maximum perfusion to the brain during CPR or severe shock, and the resultant conductive intracranial cooling lowers the oxygen demands of the individual brain cells, particularly those of the cerebrum. These two phenomena together postpone damage to brain cells in the event of cardiac arrest or severe shock. If degenerative processes have begun, cooling will thermodynamically slow them. The head cooling apparatus contains the unreacted constituents of an endothermic reaction, such as pellets of ammonium nitrate ($NH_4NO_3$) stored adjacent a selectively available reservoir of water, and thus needs no external coolants or refrigeration. Preferably, the head cooling apparatus comprises a portable self-contained system which is suitable for storage, transport and/or use anywhere.

DETAILED DESCRIPTION OF THE INVENTION

Figure 1:
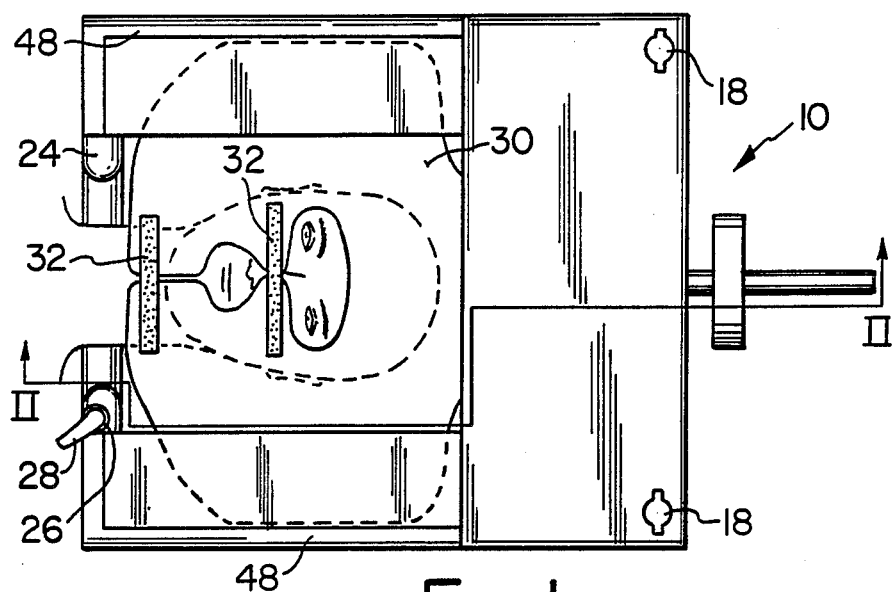
FIG. 1 is a plan view of the body of a head cooling apparatus according to the present invention, showing the head of a patient surrounded by a watertight shroud.

The present method for preventing brain damage during cardiac arrest or severe shock comprises inducing localized hypothermia in the extracranial area including the face, and optionally also including the mandible, in order to precipitate both extracranial vasoconstriction and intracranial cooling by conduction. This method of cooling the external area of the cranium without likewise cooling, for example, the torso and extremities, is moreover physiologically preferable to the more drastic induction of systemic hypothermia. In theory, although Applicant does not wish to be bound by this theory, the localized cranial cooling simplifies rewarming and minimizes "afterdrop", the continued decrease in body temperature which occurs after topical cooling means are removed. In addition, cranial cooling is preferred to systemic cooling for its obvious convenience in both in-hospital and pre-hospital patient care.

Applicant surmises an explanation, which follows, of the physiologic effects of extracranial cooling which result in neurologic preservation. Applicant does not wish to be bound by this explanation, however, because it is his method and the structure, function and result of his apparatus which constitute the present invention, not the elements of his theory.

In circulatory arrest, brain oxygen stores are exhausted within 10 seconds. (Commensurate oxygen deficiency accompanies severe shock.) Subsequent to brain anoxia, anaerobic glycolysis proceeds for approximately 4 minutes with concomitant buildup of lactic acid and exhaustion of glucose stores. Energy production thereafter ceases, causing the sodium-potassium ATPase pump to fail at the brain cell membrane. Consequent depolarization of the cell membrane permits massive calcium influx, which is thought to trigger the pathophysiology which leads to postischemic encephalopathy (PIE). Return of spontaneous circulation (ROSC), with its accompanying massive calcium sequestration from the cells, probably also contributes to intoxication of both mitochondria and smooth endoplasmic reticula, along with the formation of free radicals catalyzed by delocalized low molecular weight iron. Other aspects of pathophysiology include hypermetabolism, vasoparalysis, loss of blood-brain barrier integrity and coagulopathy.

By cooling the head, extracranial vasoconstriction increases cerebral blood flow at the same time as intracranial hypothermia retards both ATP depletion in the brain cells and subsequent membrane depolarization by thermodynamically decreasing metabolic demand. CPR-generated cerebral blood flow, maximized due to extracranial vasoconstriction, may be adequate to meet this reduced metabolic demand. If not, however, and in the event that brain cell membrane failure (depolarization) occurs despite head cooling, the hypothermia also thermodynamically inhibits the degenerative processes associated with cell membrane failure. Upon ROSC, reperfusion injury is likewise thermodynamically blunted.

In addition, because much of the ischemia-sensitive cerebral tissue is located peripherally within the cranium and is poorly insulated from the environmental temperature, Applicant believes that surface cooling of the head quickly provides therapeutic levels of hypothermia in those very areas of the brain which are most sensitive to ischemia, in addition to providing almost immediate extracranial vasoconstriction.

Although any extracranial cooling is beneficial during respiratory or cardiac insufficiency, profound head cooling is preferred. Profound head cooling is particularly preferred during cardiac or respiratory arrest, for which resuscitation time is otherwise drastically limited. (Frostbite avoidance and skin temperature monitoring may be carried out by means known in the art although, of course, frostbite is always preferable to neurologic loss.) As is impossible with induced systemic hypothermia, however, even profound cranial hypothermia is clinically feasible, due to the buffering of the cold venous return from the head by the warm venous return from the body. Apparently this buffering of cold venous return from the head is responsible for minimizing both unwanted afterdrop and undesirable myocardial and pulmonary cooling during treatment of the patient.

Although the method of cooling the exterior of the cranium, including the face and optionally the mandible, may be accomplished by a number of means, including both conductive and convective means such as conventional ice packs and the like, the preferred apparatus as claimed herein is a head cooling apparatus having the structure and function described below.

Figure 3:
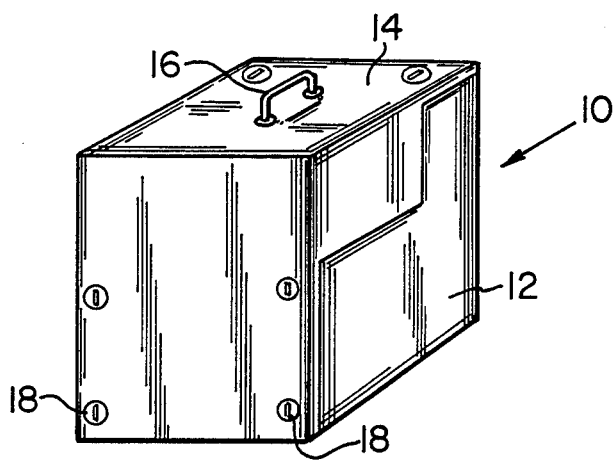
FIG. 3 is a perspective view of the head cooling apparatus having its cover section in place.

The head cooling apparatus of the present invention, shown in FIGS. 1-6, is a self-contained, portable system which enables application of cranial cooling regardless of location, whether in-hospital or at a remote location accessible only by emergency vehicle. The completely assembled head cooling apparatus is illustrated in FIG. 3; the head cooling apparatus 10 comprises a body 12 and a cover section 14. The body 12 and cover 14 are secured together by means of a plurality of latches 18. A handle 16 appends the assembled head cooling apparatus 10 for easy transport. The present invention as illustrated in FIG. 3, therefore, comprises a multi-walled carrying case.

Figure 4:
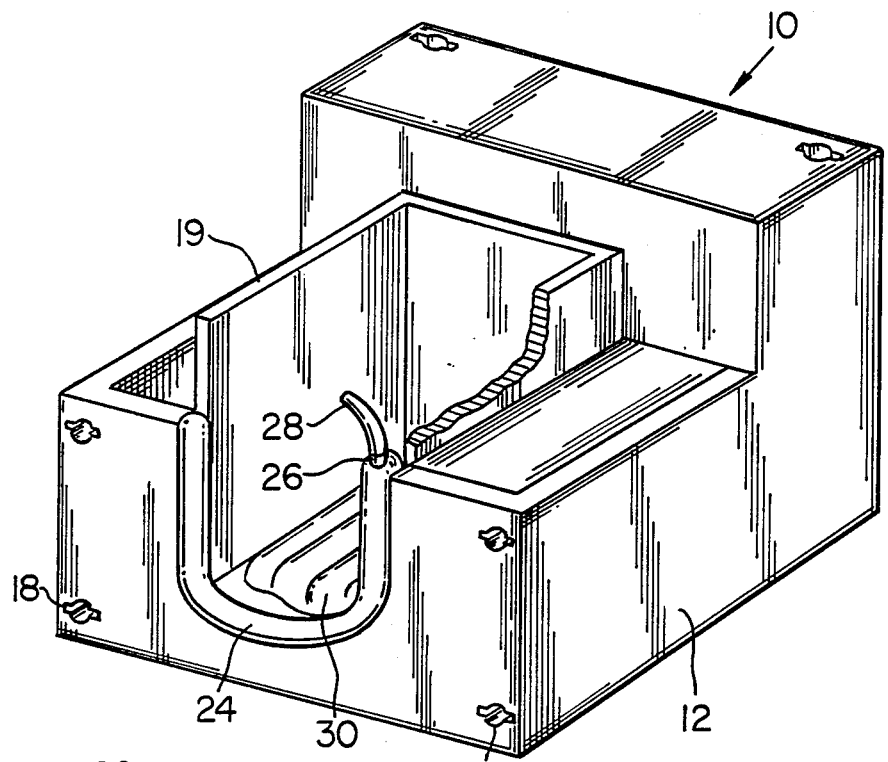
FIG. 4 is a perspective view of the body of the head cooling apparatus.
Figure 6:
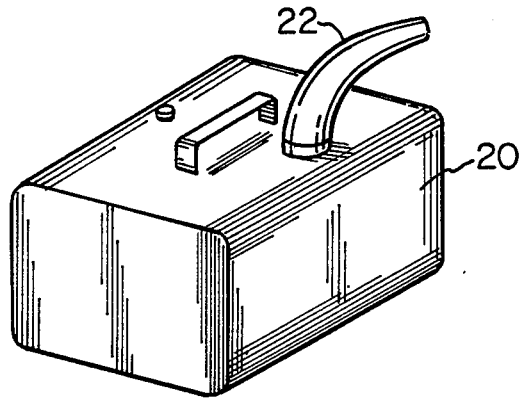
FIG. 6 is a perspective view of the water jug which is designed to fit within the cavity created by the partition shown in FIG. 4.

When the cover section 14 of head cooling apparatus 10 is removed from the body 12, by release of the plurality of latches 18, the structure shown in FIG. 4 becomes visible. FIG. 4 illustrates the body 12 of the head cooling apparatus 10, a partition 19 located centrally within the body 12, a portion of the watertight shroud 30 (discussed further below), the inflatable cuff 24, and the rotatable valve 26 and inflation nozzle 28 designed for inflation of the inflatable cuff 24. The partition 19 is a three-walled structure which rests within the body 12 of the head cooling apparatus 10 as shown, for the purpose of securing for transportation and storage purposes the water jug 20 having the spout 22 as shown in FIG. 6. Because the spout 22 rotates at its juncture with the water jug 20, the spout 22 may be rotated into a retracted position (not shown) such that the water jug 20 fits within the partition 19 for storage and travelling. FIG. 4 illustrates the partition 19 with the water jug 20 of FIG. 6 removed. The partition 19 rests atop a portion of the watertight shroud 30, a portion of which may be seen in FIG. 4.

Figure 5:
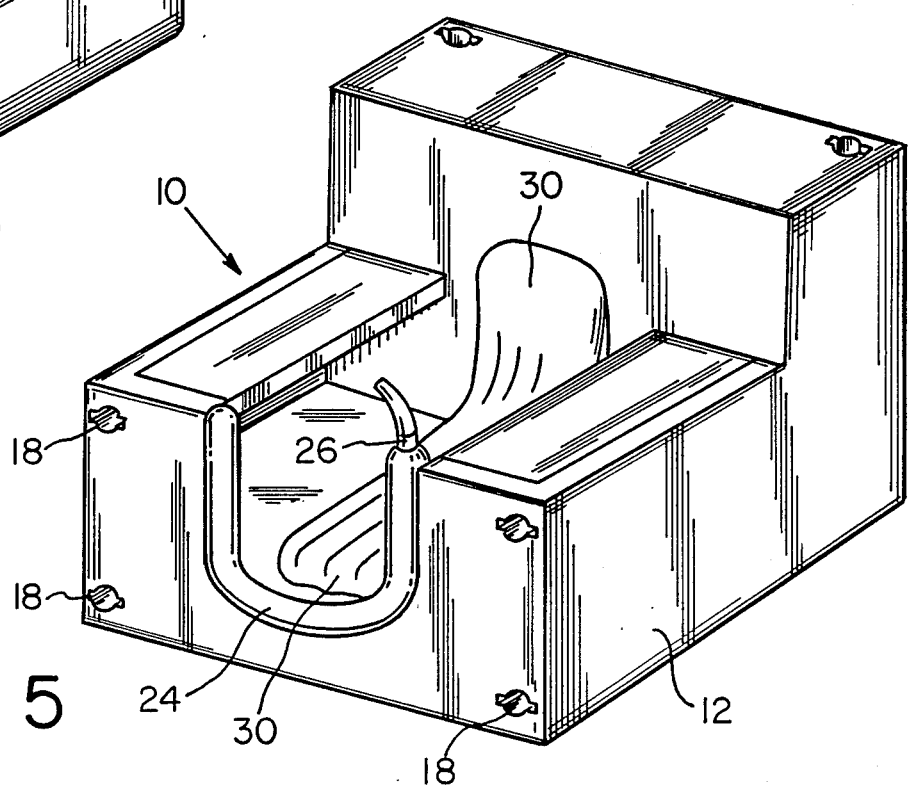
FIG. 5 is a perspective view of the body of the head cooling apparatus with the partition removed.

Because the partition 19 rests within the body 12 of the head cooling apparatus 10 but is otherwise unattached thereto, the partition is removable from the head cooling apparatus 10 just as the water jug 20 may be removed. Upon removal of the partition 19 from the body 12 of the head cooling apparatus 10, the body 12 appears as is illustrated in FIG. 5. FIG. 5 represents the same structures as illustrated in FIG. 4, but illustrates a greater portion of the watertight shroud 30. The various structures of the watertight shroud 30 are best understood when reference is made to FIGS. 1 and 2.

Figure 2:
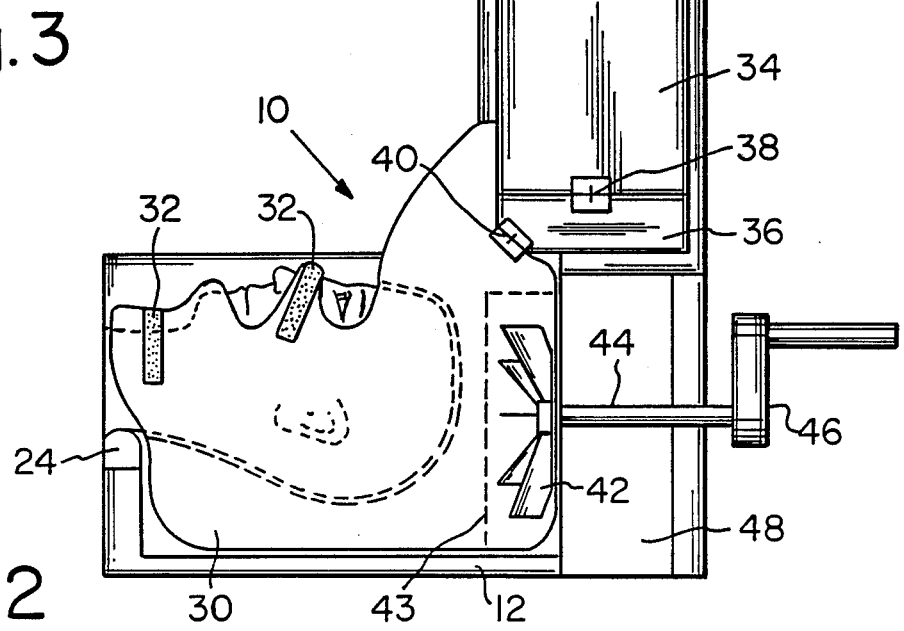
FIG. 2 is a section taken along lines II—II of FIG. 1.

Referring now to FIG. 2, the watertight shroud 30 is shown in position wrapped around the head of a patient. As shown, the watertight shroud 30 is a generally double-walled structure in which the two walls and fluid therebetween wrap from behind the patient's head up and over both sides of the patient's face, with placement of the watertight shroud 30 being effected at the nose and neck of the patient by means of shroud straps 32. (Shroud straps 32 will ordinarily be fabricated either of loop-and-latch type materials such as those sold under the trademark Velcro ®, or will consist of adhesive tabs known in the art.) More particularly, the watertight shroud 30 comprises an overall single surface of waterproof material configured to provide both an effective double walled construction and "cutout" areas for the eyes, lower nose and mouth when the watertight shroud 30 is in place. Those skilled in the art will appreciate that for appropriate medical care, health care providers must have access to the mouth, nasal airway and eyes at all times. The single surface therefore provides a generally flat, conformable, fluid-tight bag, the mouth of which is sealed to the head cooling apparatus 10 in the general area of the water reservoir 34 and the endothermic reactant reservoir 36 as illustrated.

In addition to the watertight shroud 30 illustrated in FIG. 2, FIG. 2 also illustrates the relative positions of and interconnections between the watertight shroud 30, the turbine 42, turbine shaft 44 and crank 46, and the water reservoir 34 and endothermic reactant reservoir 36. As illustrated, two entrance points into the watertight shroud 30 include the turbine shaft 44, about which the watertight shroud 30 is sealed in a suitable watertight seal, and the mouth area of the water tight shroud in the general area of the reservoirs 34, 36. To yield this structure, one portion of the mouth of the watertight shroud 30 is sealed as illustrated adjacent the reactant valve 40; the corresponding opposite segment of the watertight shroud 30 is sealed to the exterior of the water reservoir 34 and the remainder of the mouth of the watertight shroud is sealed likewise; such seals may be accomplished by means known in the art. The resultant structure is a watertight shroud 30, sealed completely at its mouth to the structures of the body 12 of the head cooling apparatus 10, which contains or encompasses two auxiliary structures: the turbine 42 and the reactant valve 40.

The water reservoir 34 is a segment of the body 12 of the head cooling apparatus 10 which contains stored water. This water may be but need not be sterile, as it does not contact the patient. Stored water is retained within the water reservoir 34 by means of water valve 38, shown in FIG. 2 in closed position. Beneath the water reservoir 34 and the water valve 38 is shown a separate chamber which comprises the endothermic reactant reservoir 36, which contains the unreacted constituents of an endothermic reaction, such as pellets of ammonium nitrate ($NH_4NO_3$). These endothermic reactants are known in the art. The water in the water reservoir 34 and the reactant in the endothermic reactant reservoir 36 therefore can provide, when admixed, coolant fluid for which no external refrigeration is required. Water and ammonium nitrate are generally employed in equal parts by weight, or at a ratio of about 1:1 by weight, and further are ordinarily incorporated into the system in the amount of 4–5 kg. each. With the combined weight of the reactants being approximately 8–10 kg., the entire system routinely weighs approximately 11–12 kg., or 25 lbs.

In operation, the disclosed and claimed head cooling apparatus 10 functions as follows. At the desired time, the water jug 20 and partition 19 are manually removed, and both the water valve 38 and the reactant valve 40 are opened. Such valve opening may be accomplished by means known in the art or, by way of example, may be effected by suitable magnets provided both on the partition 19 and as integral parts of the valves. By removal of the partition at the time the head cooling apparatus 10 is prepared for use, the movement of the partition and the force of the magnet can effect the opening of both the water valve 38 and the reactant valve 40. Those skilled in the art can easily adapt additional appropriate designs for such valves. Upon the opening of the water valve 38 and the reactant valve 40, the water stored in the water reservoir 34 passes into the endothermic reactant reservoir 36, combining with the endothermic reactant and carrying the admixed reactants into the watertight shroud 30 by force of gravity.

As the watertight shroud 30 is filling with the coolant liquid, the head of the patient may be positioned within the central cavity of the head cooling apparatus body 12. The inflatable cuff 24 is inflated, by air hose or by mouth, via the rotatable valve 26 and the inflation nozzle 28. The watertight shroud is drawn up and over the patient's head and face into the configuration as shown in FIGS. 1 and 2, with the shroud straps 32 securing the watertight shroud 30 into position. The turbine 42, having the turbine shroud 43, may be rotated by means of the crank 46 and the turbine shaft 44 to circulate the coolant within the watertight shroud 30. The coolant convection effected with the turbine 42 markedly improves cranial cooling, inasmuch as the patient's head would quickly warm the layer of coolant nearest the head if convection or fluid circulation were not provided. The turbine shroud 43, which is optional, may be fabricated of a wide variety of perforate materials including, but not limited to, stiff polymer meshes and nets.

Enhanced cranial cooling may be accomplished by actually wetting the head of the patient. The watertight shroushroud 30, of course, does not wet the patient's head, but such wetting when possible maximizes heat loss through the cranial skin and removes the air space between the head and watertight shroud, which air would otherwise function as an insulating layer. The water jug 20 is therefore provided as a part of the present head cooling apparatus 10 so that water to wet the head of the patient is available at all times, even when the present system is used in an emergency or other remote setting. Although it is not strictly necessary for the purposes of the invention, preferably the water contained in the water jug 20 will be sterile, with appropriate seals being provided at both ends of the spout 22 to maintain sterility until the seals of the spout 22 are breached.

The watertight shroud 30 of the present invention differs from prior art cold packs in that the watertight shroud is designed to cover the face as well as the top, back and sides of the head. Cooling of the face is essential to the present invention because normothermic extracranial perfusion to the face accounts for a significant portion of total extracranial perfusion, and maximum cerebral blood flow thus requires cooling of the entire extracranial area including the face. By the term "face," Applicant signifies the cartilaginous and soft tissues adjacent to and covering the anterior cranium proper; the tissues which cover the mandible need only preferably be cooled because extracranial facial perfusion concentrates in the general area of the eyes and nose.

To enhance cranial cooling, insulated areas may be provided to the present head cooling apparatus 10. For example, in FIG. 1, the insulated side walls 48 are fabricated of an insulating material; in FIG. 2, another insulated area 48 may be seen adjacent the turbine 42. Such insulating materials may include those known in the art, for example, polymer batts or foams such as Styrofoam ®, but regardless of the insulation material the material should be hermetically sealed away from any possible contact with the patient. The inflatable cuff 24 provides additional insulation and also provides for comfort and for fluid sealing in the event of wetting of the patient's head. Structures and materials for the inflatable cuff 24 are well known in the art.

Likewise known in the art are the endothermic reactants which create coolant fluids upon admixture with water. Also, those skilled in the art will recognize that the dimensions for the present head cooling apparatus are in no way critical. As an example, however, the head cooling apparatus 10 as shown in FIG. 3 may have the dimensions 2'×2'×2', or 2 feet along each side.

Suitable materials for construction of the head cooling apparatus of the present invention are many and varied. Generally, chemically inert materials suitable to contain the coolant or coolant-generating reactants are required. The watertight shroud 30 may accordingly be prepared from a wide variety of polymers, including polyurethane, polypropylene, polyethylene, polyvinyl, polyacrylic and silicone rubber sheet materials, among others, whereas the rigid structures of the present invention may be prepared of sealed wood, laminates, composites, metals and/or alloy sheet materials, etc. The watertight shroud 30 is preferably selected of a grade of polymer material which demonstrates hypoallergenicity, which material has a gauge which can withstand at least 100 lbs. pressure per square foot without failure.

The present head cooling apparatus 10 has three additional optional features. The partition 19 may rest on its opposing walls only, with the third wall containing a short cutout (i.e., 1 inch along its length) above the watertight shroud 30 resting in the bottom of the body of the head cooling apparatus 10. This configuration prevents, over time, any abrasion or compression damage which the partition 19 would otherwise exert down onto the watertight shroud 30 when the head cooling apparatus 10 is packed for storage and/or use. Second, although the fluid-filled watertight shroud 30 provides an effective "water pillow" for the head of the patient, additional hammock-like or sling structures may be fitted into the head receiving cavity of the present system to provide additional support for the head. Under ordinary circumstances with adult patients, however, such slings or additional support structures will not be necessary. Finally, the crank 46 may be hinged, for collapsed storage within the walls of the apparatus 10. The crank 46 may, of course, be fabricated of thin, strong lightweight materials which require minimal space.

Although the present method and apparatus have broad application in the emergency treatment of humans, the utility of head cooling has thus far been documented in canine studies in the laboratory. Accordingly, the following examples are illustrative.

EXAMPLE I

Twelve healthy flat-chested 12-25 kg. mongrel dogs fasted, although water was permitted, overnight. The dogs were premedicated with 10 mg./kg. body weight ketamine and were subsequently anesthetized with a gaseous admixture of nitrous oxide, oxygen and halothane. Endotrachial intubation was performed when anesthesia reached sufficient depth. Preinsult temperature was maintained between 37°-38° C. Supradiaphragmatic aortic and Swan Ganz catheters were placed via femoral cutdown. The head of each dog was shaved.

After the level of anesthesia was allowed to lighten, by allowing all dogs to breathe room air spontaneously for 4-6 minutes, ventricular fibrillation was introduced transthoracically with 100V AC. Upon confirmation of ventricular fibrillation, six dogs had their heads cooled. This was achieved by first wetting and then packing each head in ice bags. The neck of each animal was stabilized with sandbags.

Each dog was subjected to 4 minutes of ventricular fibrillation and 20 minutes of "controlled" CPR, during which sixty A-P compressions per minute were delivered by a Michigan Instruments Thumper, and one ventilation (25 cc./kg., $FIO_2 = 1.0$) was administered after every fifth compression. When initial systolic blood pressure read below 40 mm Hg, the animal was excluded from consideration. No increases in pressure of chest compression were allowed after 5 minutes of CPR.

Restoration of spontaneous circulation was then attempted by means known in the art. Rewarming was achieved by heating pads applied to the body but not the head. Median arterial pressure was maintained above 88 mm Hg using a continuous epinephrine infusion and fluid administration titrated by pulmonary artery pressors. Weaning from mechanical ventilation was begun one hour after restoration of spontaneous circulation. All dogs received 4-5 hours of intensive care, and were then returned to their cages with supplemental oxygen and maintenance IV's.

EXAMPLE II

For the dogs treated as in Example I, neurologic deficit scores (NDS) were obtained at 3, 12 and 24 hours post-resuscitation. These NDS values were assigned according to the following guidelines.

|  | Points Assigned | | Scores | |
| --- | --- | --- | --- | --- |
|  | Best | Worst | Best | Worst |
| Level of consciousness | 0 | 100 | 0 | 20 |
| Respiration | 0 | 100 | 0 | 20 |
| Cranial nerve function | 0 | 100 | 0 | 20 |

| | | | | |
|---|---|---|---|---|
| Motor and sensory function | 0 | 100 | 0 | 20 |
| Behavior | 0 | 100 | 0 | 20 |
| TOTAL | 0 | 500 | 0 | 100% |

| | |
|---|---|
| Fully awake. Can sit, feed self, stand. May have moderate motor deficit or ataxia. | 0–15% |
| Fully awake. More severe motor deficit. Cannot sit, stand, feed self. Eats when fed. Dog can right itself and stay in position. | 15–25% |
| Not awake-difficult to arouse. Some awareness off/on. Can move all limbs, but spastic. Reacts to pain. Cannot sit, stand or eat. Dog able to keep head up. Can stay in righting position, but cannot right self. Dog's position normal or a tendency for flexation with some running movements on or off. | 25–40% |
| No awareness. Often abnormal body position. Spontaneous extension of extremities. Vegetative, spontaneous running movements often with opistotonus. May exhibit spinal cord hyperreflexactivity. Vision may be severely impaired. | 40–80% |
| Totally unresponsive. Brain death or dying a cerebral death during the observation period. | 80–100% |

The head-cooled dogs had significantly better neurological outcomes than did the normothermic control dogs. Mean NDS, for the head-cooled dogs not excluded from consideration (exclusions were made for reasons well established in experimental surgical neurology), estimated at 3 hours post-ROSC, was 37.2%, whereas mean NDS for control dogs was 61.8%. Furthermore although 2 head-cooled dogs survived 24 hours (one neurologically intact and one having an NDS of only 9%), none of the control dogs survived 24 hours.

Although the invention has been described with reference to specific materials and specific processes, the invention is to be limited only insofar as is set forth in the accompanying claims.

I claim:

1. An apparatus for cranial cooling, comprising:
a watertight shroud having a permanent shape by which said shroud is adapted to extend over the forehead, face and neck as well as the top, back and sides of the head of a patient but leave uncovered the eyes, nasal airway and the mouth of the patient, said shroud including fastening means for fastening adjacent sections of said watertight shroud in the area of the face of a patient;
an endothermic reactant reservoir containing a quantity of a reactant which reacts endothermically with water; and
a water reservoir containing water, said water reservoir comprising a structural tank adjacent said shroud and above said endothermic reactant reservoir, said structural tank and said endothermic reaction reservoir having at least one valve therebetween; wherein said combined watertight shroud, structural tank and endothermic reactant reservoir contain means for fluid communication therebetween.

2. The apparatus according to claim 1 wherein watertight shroud, structural tank and endothermic reactant reservoir are mounted within a multi-walled carrying case.

3. The apparatus according to claim 2 wherein said multi-walled carrying case has a cover thereon.

4. The apparatus according to claim 3 wherein said cover has a handle thereon.

5. The apparatus according to claim 4 wherein said multi-walled carrying case includes a central cavity adjacent an inflatable cuff.

6. The apparatus according to claim 5 wherein said inflatable cuff includes a rotatable valve and an inflation nozzle adapted selectively to effect inflation of said inflatable cuff.

7. The apparatus according to claim 6 wherein a turbine is mounted within said watertight shroud.

8. The apparatus according to claim 7 wherein said turbine is mounted within said watertight shroud by means of a waterproof seal.

9. The apparatus according to claim 8 wherein said turbine is surrounded within said watertight shroud by means of a perforate turbine shroud.

10. The apparatus according to claim 9 wherein said turbine is attached to a turbine shaft and crank structurally affixed to said multi-walled carrying case.

11. The apparatus according to claim 10 wherein said multi-walled carrying case having a central cavity is adapted to store a water jug.

12. The apparatus according to claim 11 wherein said watertight shroud is fabricated of a hypoallergenic material.

13. The apparatus according to claim 1 wherein said structural tank and said reactant reservoir contain equal parts by weight of water and of said reactant which reacts endothermically with the water, respectively.

14. The apparatus according to claim 13 wherein said reactant which reacts endothermically with water is present in the amount of approximately 4–5 kg.

* * * * *

UNITED STATES PATENT AND TRADEMARK OFFICE
CERTIFICATE OF CORRECTION

PATENT NO. : 4,920,963

DATED : May 1, 1990

INVENTOR(S) : Eric W. Brader

It is certified that error appears in the above-identified patent and that said Letters Patent is hereby corrected as shown below:

Column 2 Lines 9-10 "prehos-pital" should read --pre-hospital--.

Column 4 Line 38 before "shown" insert --as--.

Column 6 Line 56 "shroushroud" should read --shroud--.

Claim 2 Lines 13-14 Column 10 before "watertight" insert --said--.

Signed and Sealed this

Thirteenth Day of August, 1991

Attest:

HARRY F. MANBECK, JR.

*Attesting Officer*

*Commissioner of Patents and Trademarks*